United States Patent [19]

Mannear

[11] 4,032,662

[45] June 28, 1977

[54] METHOD FOR THE TREATMENT OF CONTACT ALLERGIC DERMATITIS

[75] Inventor: Idabelle K. Mannear, Montrose, Pa.

[73] Assignees: Idabelle K. Mannear; Charles H. Mannear, both of Montrose; George W. Kanarr; Ruth A. Kanarr, both of Shavertown, all of Pa. ; part interest to each

[22] Filed: Jan. 5, 1976

[21] Appl. No.: 646,728

[52] U.S. Cl. .............................................. 424/331
[51] Int. Cl.² ........................................ A61K 31/12
[58] Field of Search ................................... 424/331

[56] References Cited

UNITED STATES PATENTS 3,862,331  1/1975  Crary .................................. 424/331

OTHER PUBLICATIONS

Merck Index (1960) 7th Ed., pp. 7–8.

*Primary Examiner*—Stanley J. Friedman
*Attorney, Agent, or Firm*—Pollock, Vande Sande & Priddy

[57] ABSTRACT

A method for the treatment of contact allergic dermatitis, particularly plant contact dermatitis such as poison ivy, which comprises the topical application of acetone to the affected areas.

7 Claims, No Drawings

METHOD FOR THE TREATMENT OF CONTACT ALLERGIC DERMATITIS

BACKGROUND OF THE INVENTION

The present invention is related to a topical treatment of contact allergic dermatitis including poison ivy.

A large segment of the population has suffered at one time or another from contact allergic dermatitis, and particularly from plant contact allergic dermatitis such as poison ivy. Poison ivy is one of the more common types of plants which cause plant contact allergic dermatitis, and many different types of preparations have been suggested to relieve its symptoms. Most provide, at best, only partial relief and then only after repeated applications. Other suggested treatments are recognized as being effective only if applied promptly after exposure to the particular agent causing the allergic reaction, and thus their usefulness is limited since the patient in most instances becomes aware of his having been exposed to the plant or the like after the appearance of a rash and the onset of itching. Some of the more effective treating compositions such as the steroids are normally only recommended in extreme cases because they may exert actions on parts of the body in addition to the areas affected with the dermatitis.

Certain preparations including those in the form of injectable compositions have been suggested as a prophylaxis to prevent contact allergic dermatitis. However, these prophylaxis treatments are not effective in treating a patient already suffering from contact allergic dermatitis.

One suggested treatment for plant contact allergic dermatitis is the thorough scrubbing of irritated parts with benzine followed by rinsing with alcohol. Another treatment includes washing with alcohol substantially immediately after contact as discussed in Berman et al, "Common Skin Diseases", Second Edition. However, treating with alcohol is not effective after a rash or blistering has developed.

Another suggested treatment involves the washing of the affected areas substantially immediately after contact with certain "laundry bar soaps" available under the trade designations "Fels-Naphtha" and "Octagon", but here again the disadvantage of any such treatment is the requirement that the patient actually be aware of his having been exposed to the allergic substance.

SUMMARY OF THE INVENTION

A considerable amount of continuing work is being done to develop new methods for treating contact allergic dermatitis and particularly plant contact allergic dermatitis. It is accordingly an object of the present invention to provide a treatment for contact allergic dermatitis. A further object of the present invention is to provide a treatment which merely requires the topical application to the affected areas.

A further object of the present invention is to provide a method of treatment which is effective, easy to carry out, and relatively inexpensive.

The present invention is directed to a method for treating a patient suffering from contact allergic dermatitis which comprises topically contacting affected areas of the patient's skin with acetone.

DESCRIPTION OF PREFERRED EMBODIMENTS

In accordance with the present invention, it has been discovered that acetone can be applied topically to affected areas of the skin of a patient suffering from contact allergic dermatitis, and thereby successfully reduce and eliminate the rash, blistering, and severe itching which normally accompanies the dermatitis. The use of acetone provides a process which is substantially more effective, and provides for quicker alleviation of the patient's distress than the more complex topical applications heretofore suggested. Furthermore, as will be shown in the examples hereinbelow, the treatment with the acetone is sufficient to completely cure the dermatitis.

The experimentation conducted thus far clearly establishes that acetone, even when employed as the sole treating agent, is effective in treating contact dermatitis. Of course, it is recognized that other ingredients which do not adversely affect the treatment to any undesirable degree and which do not render the acetone ineffective can be employed in conjunction with the acetone. It has been noted, however, that various oils such as those present in certain nail polish remover compositions as additions with the acetone normally present have adversely affected the function of the acetone as a treating agent for contact allergic dermatitis.

The amount of acetone employed for the treatment is not especially critical and needs to be merely that amount sufficient to at least reduce the suffering and particularly the itching. Usually, the acetone is applied liberally to the irritated or affected areas so as to thoroughly cover the irritated areas. Preferably, the acetone is applied using absorbent cotton with a rubbing motion over the affected skin areas.

In order to further illustrate the present invention, the following testing on various patients which has been carried out over the last few years is presented hereinbelow.

EXAMPLE 1

The patient was a young adult woman who had been exposed to poison ivy. At the time of treatment, the patient had severe poison ivy reaction on her hand to the extent that the skin had cracked open and was inflamed. The affected areas were treated with absorbent cotton which had been moistened with acetone. Within a few minutes, the patient stated that the itching had stopped completely. Only one application of the acetone was made. The inflammation quickly subsided, and within a few days the cracks in the skin had healed.

EXAMPLE 2

The patients were three young children. All three were covered over substantial portions of their bodies with welts from poison ivy. After treatment of the affected areas which acetone, all three patients experienced prompt relief and were virtually completely cured by the next day.

EXAMPLE 3

The patient was a young boy residing in Florida who was allergic to the skin of the mango fruit. At the time of treatment, the patient's entire face itched and his eyelids were almost swollen shut. Acetone was applied to the affected areas with prompt relief, and the patient was substantially fully recovered by the next day.

EXAMPLE 4

The patient was a male adult. The patient had a severe itching rash on his hands which he had apparently obtained from handling a Christmas tree in his home. The patient's hands were thoroughly cleansed with acetone. Virtually instant relief was experienced and by the following day the inflammation had disappeared.

EXAMPLE 5

The patient was a young female who had an itching rash on her legs as a result of contact with poison ivy. Acetone was applied with prompt cessation of itching. The affected areas were devoid of any irritation within about a day.

None of the patients treated suffered any adverse side effects.

As illustrated by the above examples, the use of acetone is effective in treating contact dermatitis due to allergic reactions to a number of different substances including plants of the Anacardiacea family. Surprisingly, the acetone, as contrasted to the prior use of alcohol, is effective after the patient's skin has become blistered or irritated. Moreover, the above examples illustrate that acetone can be an effective treatment. The present invention is effective with only a single topical application of acetone.

In addition to the absence of adverse side effects in the testing conducted to date, the safeness of applying acetone to the skin at least in the amounts found to be needed to treat contact allergic dermatitis is evidenced by the Merck Index, Eighth Edition, 1968, P. 7; "Comparative Acute Effects of Some Chemical on the Skin of Rabbits and Guinea Pigs," Roudabush et al, Toxicology and Applied Pharmacology, 7, 559–65 (1965); "An Electron Microscopic Study of Human Epidermis after Acetone and Kerosene Administration", J. Invest. Dermatol., 60: 33–45, January 1973; Hodge and Stermer, 1949, Tabulation of Toxicity Classes, AM IND. HYG. ASSOC. Quart. 10: 93–96; and Some Data on The Toxic Properties of Acetone, Gig. Tr. Prof. Azool, 6: 56, September 1962.

In addition to the pharmaceutical uses of acetone discussed in the Merck Index, reference has been made in some of the literature to the use of acetone or ether for the extraction of the "active principal" causing poison ivy, i.e., a substance known as Urushial. The acetone was recited for such use in view of its effectiveness as an organic solvent. Extracts are apparently obtained in this manner from poison ivy leaves to be used for desensitization studies of patients who are reactive to poison ivy. Nevertheless, the various prior uses of acetone do not suggest that acetone can effectively treat contact dermatitis, after the skin has become irritated or has developed a rash.

Other discussions of interest for the sake of background material can be found in "Antiviral Affect of Acetone," J. Gen. Viral. 3: 271–73, September 1968, and "The Antibacterial Action of Human Skin. Invivo Affect of Acetone Alcohol and Soap on Behavior of Stap. Queres.", Brit. J. Exp. Path. 49: 209–15, April 1968.

What is claimed is:

1. A method for the treatment of a patient afflicted with contact allergic dermatitis which comprises topically applying acetone to the affected areas of the skin of said patient.

2. A method in accordance with claim 1 wherein said contact dermatitis is characterized by visible irritation and blistering of said affected areas of the skin.

3. A method in accordance with claim 1 wherein said treatment comprises a single topical application of acetone.

4. A method in acordance with claim 1 wherein said contact allergic dermatitis is plant contact allergic dermatitis.

5. A method in accordance with claim 4 wherein said plate contact allergic dermatitis is caused by contact with poison ivy.

6. A method in accordance with claim 4 wherein said plant contact allergic dermatitis is caused by contact with the skin of the mango fruit.

7. A method in accordance with claim 4 wherein said plant contact allergic dermatitis is caused by contact with a plant of the Anacardiacea family.

* * * * *